US012654000B2

(12) United States Patent
Richert et al.

(10) Patent No.: US 12,654,000 B2
(45) Date of Patent: Jun. 16, 2026

(54) METHOD FOR PRODUCING A BEARING ARRANGEMENT FOR AN IMPLANTABLE BLOOD PUMP, BEARING ARRANGEMENT AND IMPLANTABLE BLOOD PUMP

(71) Applicant: Berlin Heart GmbH, Berlin (DE)

(72) Inventors: Hendryk Richert, Berlin (DE); Oliver Peters, Berlin (DE)

(73) Assignee: Berlin Heart GmbH, Berlin (DE)

( * ) Notice: Subject to any disclaimer, the term of this patent is extended or adjusted under 35 U.S.C. 154(b) by 711 days.

(21) Appl. No.: 17/296,884

(22) PCT Filed: Nov. 26, 2019

(86) PCT No.: PCT/EP2019/082639
§ 371 (c)(1),
(2) Date: May 25, 2021

(87) PCT Pub. No.: WO2020/109338
PCT Pub. Date: Jun. 4, 2020

(65) Prior Publication Data
US 2022/0023613 A1 Jan. 27, 2022

(30) Foreign Application Priority Data

Nov. 27, 2018 (EP) ..................................... 18208492

(51) Int. Cl.
*A61M 60/82* (2021.01)
*A61M 60/17* (2021.01)
(Continued)

(52) U.S. Cl.
CPC .......... *A61M 60/237* (2021.01); *A61M 60/17* (2021.01); *A61M 60/178* (2021.01);
(Continued)

(58) Field of Classification Search
CPC .. A61M 60/422; A61M 60/82; A61M 60/237; A61M 60/81
See application file for complete search history.

(56) References Cited

U.S. PATENT DOCUMENTS

2005/0135948 A1    6/2005   Olsen et al.
2014/0066691 A1*   3/2014   Siebenhaar ......... A61M 60/422
                       600/16

FOREIGN PATENT DOCUMENTS

EP       3 300 749 A1    4/2018
WO    WO 00/32257 A1   6/2000
(Continued)

OTHER PUBLICATIONS

International Search Report for Application No. PCT/EP2019/082639, dated Mar. 27, 2020, European Patent Office, Rijswijk, Netherlands, pp. 1-5.

*Primary Examiner* — Jennifer Pitrak McDonald
*Assistant Examiner* — Jennifer L Ghand
(74) *Attorney, Agent, or Firm* — Crowell & Moring LLP

(57) ABSTRACT

A method is provided for producing a bearing arrangement for an implantable blood pump. A bearing arrangement and an implantable blood pump are also provided. In the method, a rotor may be provided having one or more drive magnets. The rotor has a conveying element. In addition, a stator having stator windings is provided. Furthermore, the rotor is arranged in a flow channel formed by an inside wall of the stator. A rotor rotation is then driven. While the rotor rotation is driven, a deflection of the rotor is determined. In addition, the deflection of the rotor may be corrected by applying, removing, magnetizing and/or demagnetizing magnetically active material on the stator and/or on the rotor in a non-rotationally symmetrical manner.

12 Claims, 3 Drawing Sheets

(51) Int. Cl.
    *A61M 60/178*      (2021.01)
    *A61M 60/216*      (2021.01)
    *A61M 60/237*      (2021.01)
    *A61M 60/422*      (2021.01)
    *A61M 60/538*      (2021.01)
    *A61M 60/81*      (2021.01)
    *A61M 60/822*      (2021.01)

(52) U.S. Cl.
    CPC ........ *A61M 60/216* (2021.01); *A61M 60/422*
        (2021.01); *A61M 60/538* (2021.01); *A61M*
        *60/81* (2021.01); *A61M 60/82* (2021.01);
        *A61M 60/822* (2021.01); *A61M 2205/3317*
        (2013.01); *A61M 2205/3365* (2013.01)

(56)                 References Cited

FOREIGN PATENT DOCUMENTS

WO      WO 2014/036416 A1      3/2014
WO      WO 2018/213666 A1      11/2018

* cited by examiner

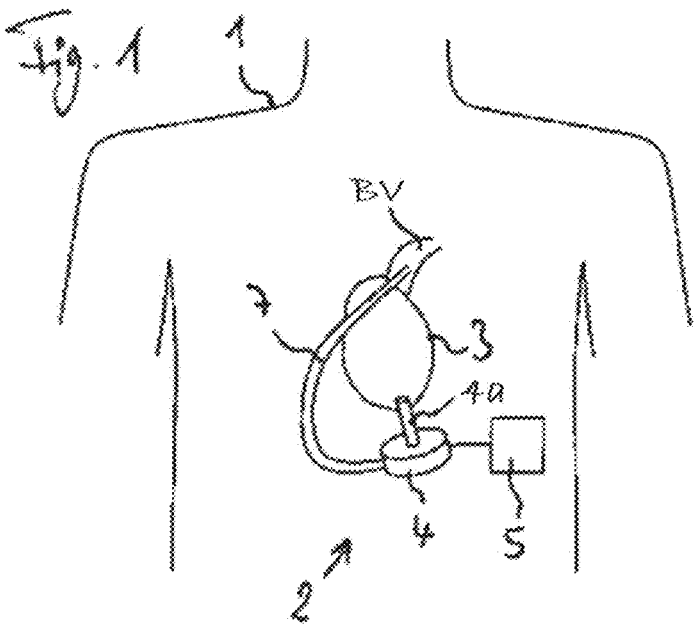
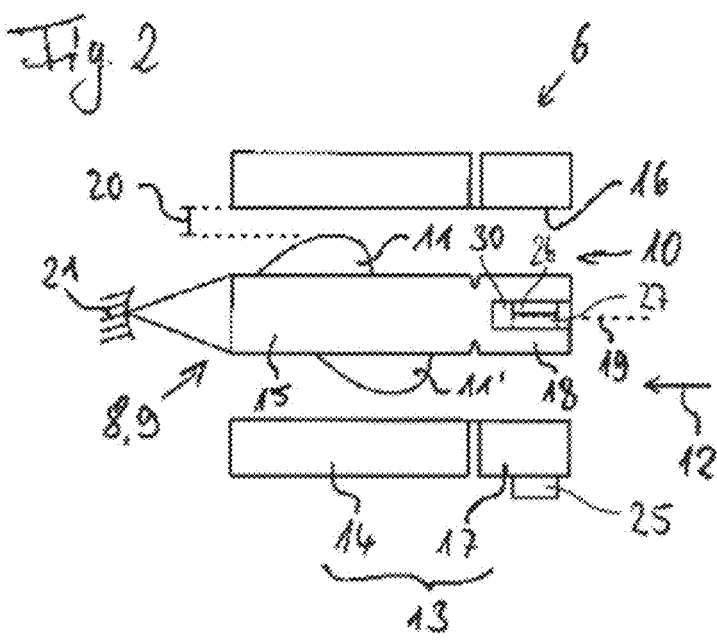

METHOD FOR PRODUCING A BEARING ARRANGEMENT FOR AN IMPLANTABLE BLOOD PUMP, BEARING ARRANGEMENT AND IMPLANTABLE BLOOD PUMP

CROSS-REFERENCE TO RELATED APPLICATIONS

This application is a 371 nationalization of international patent application PCT/EP2019/082639 filed Nov. 26, 2019, which claims priority under 35 USC § 119 to European patent application EP 18 208 492.1 filed Nov. 27, 2018. The entire contents of each of the above-identified applications are hereby incorporated by reference.

TECHNICAL FIELD

The present application lies in the field of medical engineering and in particular in the field of implantable blood pumps for assisting cardiac function. The application relates to a method for producing a bearing arrangement for an implantable blood pump, a bearing arrangement, and an implantable blood pump.

BRIEF DESCRIPTION OF THE DRAWINGS

In the figures:

FIG. 1 shows a schematic view of a blood pump which is implanted in a patient's body;

FIG. 2 shows a schematic view of an electric motor of the blood pump;

DETAILED DESCRIPTION

Figures 3A, 3B, 3C:
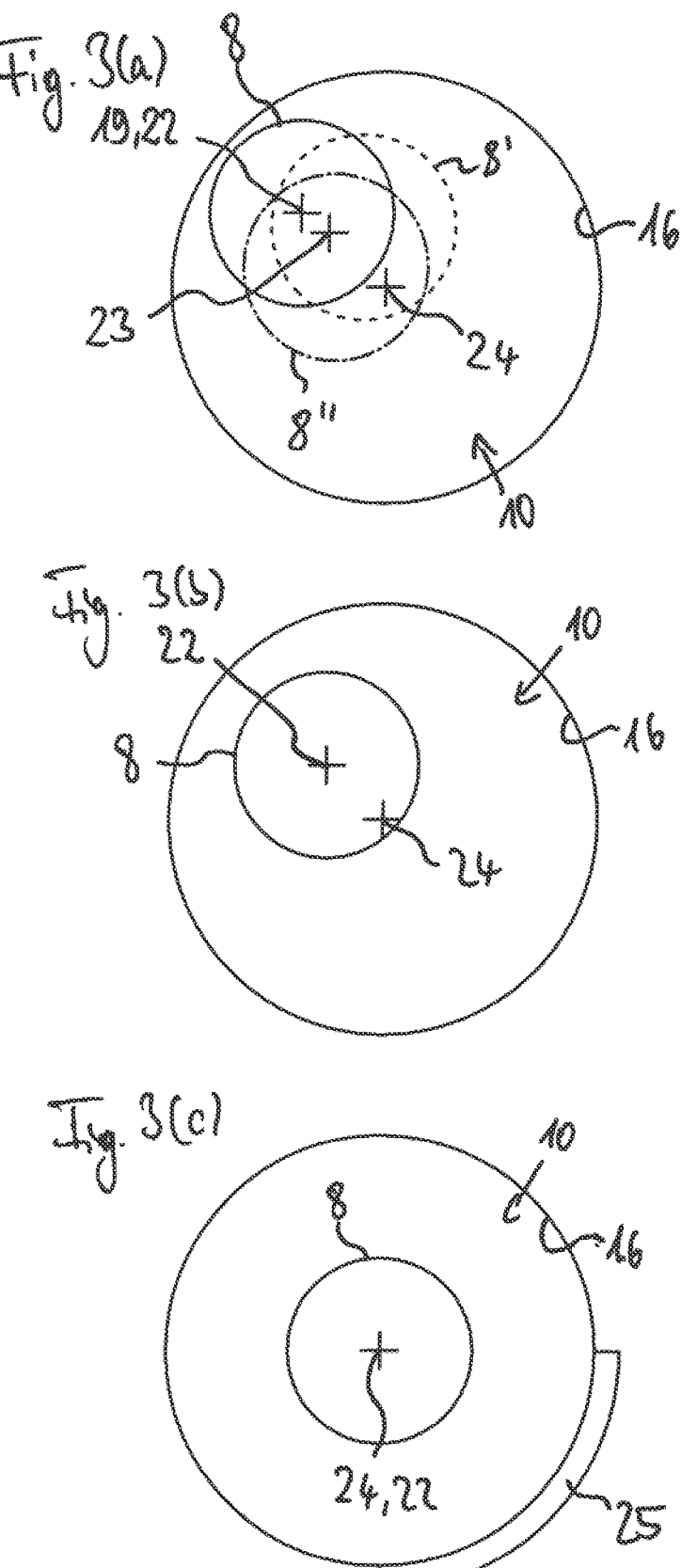
FIGS. 3(A) to (c) show schematic views to illustrate various method steps in the production of the blood pump.

Blood pumps are known from the prior art. These blood pumps may be used if the cardiac function of a patient needs to be assisted or replaced. Conventional systems that are used in this regard are what are known as VADs (ventricular assist devices). Heart pumps of this kind may be embodied, for example, as what are known as an LVAD (left ventricular assist device), RVAD (right ventricular assist device), or BiVAD (bi-ventricular assist device). Besides the blood pump, which is implanted in the patient during operation, these systems generally also comprise a control unit, which for example is arranged outside the patient's body and is connected to the blood pump by a cable (driveline). The blood pump generally comprises a motor with a stator and with a rotor, which is provided with a blading and is arranged in a flow channel of the blood pump. The motor of the blood pump may be driven by energy delivered by the control unit, for example in that a flow of current is generated in windings of the stator, as a result of which the rotor together with its blading is set in rotation in order to pump the patient's blood.

In particular in the case of blood pumps with magnetic bearing, which have a relatively small gap between the blading of the rotor and an inner wall of the flow channel, this being applicable in particular for axial and semi-axial flow geometries, a precisely controllable position of the rotor in the flow channel of the blood pump may be necessary for reliable functioning of the blood pump. For example, document EP 3 300 749 A1 describes a blood pump with a rotor that has a radial passive magnetic bearing. If a precise setting of the rotor position is necessary, production of the magnetic bearing of the blood pump may be relatively complex, since permanent magnets used as the starting material for the magnetic bearing generally may have magnetic properties with a tolerance that is not insignificant. In order to produce a blood pump with a precisely set rotor position, for example a plurality of permanent magnets may be incorporated in the blood pump, tested in respect of their magnetic properties, and swapped until the desired magnetic properties are provided. However, such a process is relatively complex and will lead to increased waste.

An object of the present invention is to propose an improved method for producing a bearing arrangement for an implantable blood pump. In particular, the proposed method shall be relatively quick and economical and shall allow production of a blood pump with which the magnetic properties and the rotor position are precisely set. In addition, an object of the present application is to propose an accordingly advantageous bearing arrangement as well as an accordingly advantageous implantable blood pump.

In the proposed method for producing a bearing arrangement for an implantable blood pump, a rotor having one or more drive magnets is provided. The rotor has a conveying element. In addition, a stator with stator windings is provided. Furthermore, the rotor is arranged in a flow channel formed by an inner wall of the stator. Blood is pumped through the flow channel when the blood pump is implanted and operated. The rotor is driven in rotation, in particular by generation of a flow of current in the stator windings. During the production process, the rotor is driven in rotation and at the same time a deflection of the rotor is determined. In a further step, the deflection of the rotor is corrected by non-rotationally symmetrical application, removal, magnetization and/or demagnetization of magnetically active material on the stator and/or on the rotor. The bearing arrangement, in some embodiments, may be part of an electric motor of the blood pump which additionally comprises the stator and the rotor.

By means of the proposed method, bearing arrangements for blood pumps which allow precise positioning of the rotor during operation may be produced. These bearing arrangements thus run very smoothly and are thus durable and energy-efficient. In addition, the pump may be operated over a broader working range if the rotor is positionable exactly in its neutral position. By means of the method steps of determining the deflection of the rotor, any magnetic unbalance possibly present and caused by the stator and rotor magnets used can be defined and then corrected in a targeted manner. The determination of the deflection of the rotor is understood to mean the determination of a position or a distance or an angle of the rotor relative to a reference point or a reference axis. As a result of this step, in comparison to production methods in which a plurality of different rotor and/or stator magnets are tested and selected, blood pumps having the desired magnetic properties are thus producible with little waste and therefore in a material-saving and economical manner. A further advantage is that the rotors and stators magnetically corrected by the proposed method, at the point of final assembly, generally do not require any further measures for correcting the magnetic properties, such that subsequent steps in the production of the electric motor or the blood pump may be performed relatively quickly and easily. The present application may additionally relate to a method for producing the blood pump, which method comprises the method steps for producing the bearing arrangement.

Since the present method is a production method and not an operating method, the deflection may be corrected already prior to operation of the blood pump, in particular once and/or permanently. The application, removal, magnetization and/or demagnetization of magnetically active material on the stator and/or on the rotor is generally permanent or remains permanently. In particular, the magnetically active material may be permanently magnetized and/or demagnetized in the event of a correction according to the proposed production method. In typical embodiments, the magnetic material therefore is not a conductor through which current is passed, in particular is not a coil through which current is passed. In some embodiments, there is no longer any need for a readjustment, in particular a permanent readjustment, during operation of the blood pump. Since the present method is a production method, the described method steps are generally not carried out in the body of a human or animal. Following the correction, it is generally provided that a blood pump containing the corrected bearing arrangement is delivered. Additionally or alternatively, in particular prior to the delivery, it may be provided that a, or the, blood pump containing the corrected bearing arrangement is packaged in a sterile manner. It is preferably provided that the bearing arrangement forms a passive magnetic bearing. In this way, a simpler construction of the bearing arrangement is achieved. In addition, the production method described above and below is particularly suitable for correction in the case of passive magnetic bearings, since these have permanent-magnetic properties which may be corrected particularly effectively already during the production process. In preferred embodiments, the magnetically active material is applied, removed, magnetized or demagnetized to or from or on the rotor during the correction, as described below in greater detail.

It is provided in preferred embodiments that the bearing arrangement comprises a magnetic radial bearing with at least one rotor bearing magnet and at least one stator bearing magnet. The deflection of the rotor may be a radial deflection. In addition, it may be provided that the radial deflection of the rotor is determined as the rotor is being driven in rotation. The radial deflection may then be corrected as described above or below. In this case, the radial deflection is generally reduced, for example with respect to a center point or a cylinder axis of symmetry of the flow channel. In this way, precise control of the gap in the flow channel between stator and rotor is made possible.

The rotation properties of the rotor are dependent on a speed at which the electric motor is operated. In this case, the rotor may rotate about its magnetic center-of-gravity axis at a sub-critical (low) speed (below the resonant frequency) and may perform a wobbling movement and may rotate about its axis of inertia at a super-critical (high) speed (above the resonant frequency).

In some embodiments, the radial deflection is determined whilst the rotor is being driven in rotation at a speed at which the rotor rotates substantially about its axis of inertia. The radial deflection of the rotor may then be reduced by non-rotationally symmetrical application, removal, magnetization and/or demagnetization of magnetically active material on the stator.

The reference point for determining the deflection maybe, in this case, for example, a center point or cylinder axis of symmetry of the flow channel. Following the correction, a geometric center-of-gravity axis of the rotor, for example, may coincide with the cylinder axis of symmetry of the flow channel, so that the rotor, in a working region, lies substantially centrally in the flow channel or rotates.

In this case, the deflection is determined at a relatively high speed, at which the rotor rotates about its axis of inertia in a self-stabilised manner. The position of the rotor is in this case normally stable, so that the deflection is independent of time. The position of the rotor is in this case generally influenced primarily by the magnetic field of the stator bearing magnet. A precise setting of the rotor position may thus be achieved by the correction at the stator. When determining its deflection, the rotor is typically operated in the super-critical state. The resonance speed above which the rotor is operated super-critically is generally geometry-dependent and may be, for example, at least 2000 rpm, in particular in radial pump systems more than 3000 rpm, and in particular in axial pump systems more than 6000 rpm.

It may be provided additionally or alternatively that the radial deflection is determined whilst the rotor is being driven in rotation at a speed at which the rotor rotates substantially about its magnetic center-of-gravity axis. The deflection of the rotor may then be corrected by non-rotationally symmetrical application, removal, magnetization and/or demagnetization of magnetically active material on the rotor.

In this case, the deflection of the rotor is generally determined at low speeds, at with the rotor rotates about its magnetic center of gravity and at which the deflection of the rotor is therefore time-dependent, so that the rotor performs a kind of wobbling movement or vibratory movement. In this case, the rotor position may be controlled particularly efficiently by correction of the magnetic unbalance at the rotor. The deflection is then determined generally in the sub-critical operation at speeds of at most 500 revolutions per minute. The correction of the magnetic unbalance that the rotor is generally performed such that the rotor then rotates in a stable manner with constant radial deflection over time.

In some embodiments, in order to precisely set the magnetic properties of the bearing arrangement or of the electric motor, the correction under sub-critical conditions is firstly performed, followed by the correction under super-critical conditions.

For example, in some embodiments it may be provided that a liquid is arranged in the flow channel between stator and rotor as the rotor is being driven in rotation. The measurement is therefore performed approximately under actual operating conditions, in which blood is arranged in the flow channel and is pumped through said channel.

The deflection of the rotor whilst the rotor is being driven in rotation may be determined, for example, in a particularly simple way by means of microscope and/or by means of distance sensors and/or by means of acceleration sensors.

In typical embodiments, the deflection of the rotor by application of a magnetizable and/or magnetized material is corrected. This material may be, in particular, a permanent-magnetic or soft-magnetic material, for example NdFeB or sheet iron or a soft-magnetic alloy. The correction may thus be performed easily, in a foreseeable manner, and particularly expediently. This is true in particular when the correction is performed on the stator, since in this case there is no need to take into consideration any existing or generated mechanical unbalances.

For example, it may be provided that the deflection of the rotor is corrected by non-rotationally symmetrical application or removal of magnetically active material at the rotor. In this case, magnetically inactive material, for example non-magnetic stainless steel or brass, may advantageously additionally be removed from the rotor or applied to the rotor to correct a mechanical balance of the rotor.

The mechanical unbalance may be caused, for example by the magnetic correction of the deflection of the rotor. For example, the magnetically inactive material may be removed from the rotor or applied to the rotor in such a way that an influence of the magnetic correction on the axis of inertia of the rotor is compensated. It is thus possible to stop the magnetic correction from accidentally generating mechanical unbalances, which, in the case of a correction at the rotor, thus contributes to an increase in the smooth running.

If the magnetically inactive material is applied to the rotor to correct a mechanical balance of the rotor, said material may be applied to an opposite side of the rotor, for example with respect to an axis of inertia of the rotor and with respect to magnetically active material applied non-rotationally symmetrically to the rotor. The magnetically inactive material may have, for example, substantially the same density or a similar density as the magnetically active material, whereby the correction of the mechanical unbalance is particularly simple. For example, the magnetically active material may contain substantially iron, and the magnetically inactive material may contain substantially non-magnetic, in particular anti-ferromagnetic stainless steel. In other embodiments, the magnetically active and the magnetically inactive material may be differently filled polymers, for example. Different densities of magnetically active and magnetically inactive compensation material may be compensated, for example, by purposefully unequal profiles of the materials. By applying the magnetically inactive material, the geometric axis of symmetry of the rotor is generally brought into conformity with its axis of inertia. Magnetically active and/or magnetically inactive material may be removed, for example in a precise manner, by sanding.

In some embodiments, the deflection of the rotor is corrected by non-rotationally symmetrical magnetization or demagnetization of magnetically active material of the rotor. In this case, generally no local mass change is produced. In this way, the magnetic correction of the rotor therefore does not accidentally cause a mechanical unbalance. The magnetization or demagnetization may be performed, for example, thermally and optionally under application of a magnetic field. For example, the magnetically active material may be heated locally above the Curie temperature of the material using a laser or a soldering iron.

The present application also relates to a correspondingly advantageous bearing arrangement for an implantable blood pump. The bearing arrangement may be produced by a method as described above or below. In addition, the present application relates to a correspondingly advantageous implantable blood pump. The blood pump may comprise the electric motor with the rotor and the stator. In addition, the blood pump may comprise the bearing arrangement with the passive magnetic radial bearing comprising the rotor bearing magnets and optionally further rotor bearing magnets and the stator bearing magnets and optionally further stator bearing magnets. The blood pump may additionally comprise a magnetically active material applied non-radially symmetrically to the rotor and/or to the stator to define and/or correct a radial deflection of the rotor. The radial deflection of the rotor is typically defined or corrected in such a way that the geometric center-of-gravity axis of the rotor coincides with the cylinder axis of symmetry of the flow channel or is biased in a certain direction in accordance with the force conditions during the operation of the pump.

The magnetically active material may be soft-magnetic or permanent-magnetic, for example. In some embodiments the magnetically active material is soft-magnetic strip for example, which in particular is applied from outside to part of the stator. In other embodiments the magnetically active material may be a magnetically active bar, in particular a half-round bar, for example an iron bar, which is provided on the rotor, in particular in an inner recess of the rotor. For the strip or the bar it is particularly reliably foreseeable how strong a magnetic correction of the deflection is brought about by what length and thickness.

The implantable blood pump may also comprise a magnetic axial bearing, in particular a passive magnetic axial bearing. As a result of this bearing, the rotor may be magnetically biased in the axial direction, for example in that the rotor is pressed against a bearing face of a contact bearing, for example a spherical or aspherical ball or tapered roller bearing.

The deflection of the rotor is generally corrected in such a way that a gap between the rotor, in particular the blading, and an inner wall of the stator, in particular running fully around the rotor, is at least 20 and/or at most 500 μm.

In the proposed method it is generally the case that a certain amount of the magnetically active material of the rotor or of the stator is maintained during the correction. In particular, it may be provided that at least 50, in particular at least 80 vol. % of the magnetically active material of the stator or rotor and in particular of the stator bearing magnet(s) or of the rotor bearing magnet(s) is maintained with unchanged magnetic properties during the correction. For example, a complete exchange of the stator bearing magnet or rotor bearing magnet therefore is not normally provided.

Features described above or below in respect of the production method are applicable accordingly to the bearing arrangement and/or to the blood pump, and vice versa.

Embodiment examples will be described hereinafter with reference to the figures.

FIG. 1 shows schematically a body 1 of a patient, in which a blood pump 2 for assisting the functioning of the heart 3 is implanted. The blood pump 2 has a motor, which is typically embodied as an electric motor with a rotatable conveying element and which is received in a pump housing 4 of the blood pump 2. The pump housing 4 is connected to a control unit 5, which likewise may be implanted, as is shown schematically. The control unit 5, in some embodiments, may be received fully or partially likewise in the implanted pump housing 4. In other embodiments, the control unit 5 is arranged outside the body. The pump housing 4 additionally comprises an inlet channel 4a, which is connected to an inlet cannula of the pump housing 4 and by means of which blood may be removed from a chamber of the heart 3 and conveyed via a cannula 7 into a blood vessel BV. The control unit 5 is designed to control the motor of the blood pump 2 to pump the blood.

FIG. 2 shows a schematic depiction of the electric motor 6 of the blood pump 2. Recurrent features in this figure and in the following figures are provided with like reference signs. The electric motor 6 is received in the pump housing 4 and comprises a rotor 8 and a stator 13. The rotor 8 has the rotatable conveying element 9 or forms said element. A flow channel 10 is delimited by an inner wall 16 of the stator 13, which inner wall is substantially cylindrical in the shown region, and blood is pumped through the flow channel during operation of the blood pump 2. The rotor 8 or the conveying element 9 comprises a blading 11, 11' for conveying the blood for example in a direction opposite the direction of the arrow denoted by reference sign 12, and in the direction of the cannula 7 shown in FIG. 1. In order to rotate the rotor 8 so as to pump the blood, a flow of current controlled electronically by the control unit 5 is generated in windings 14 of the stator 13. A drive magnet 15 of the rotor 8, which magnet may be embodied for example as a permanent magnet and is typically rigidly connected to the rest of the parts of the rotor 8 and in particular to the blading 11, 11', may be set in rotation by the magnetic field generated by the flow of current in the windings 14.

The electric motor 6 additionally comprises a bearing arrangement with a magnetic radial bearing, which for example may be embodied as a passive bearing and may have one or more stator bearing magnets 17 and one or more rotor bearing magnets 18. The stator bearing magnet(s) 17 and the rotor bearing magnet(s) 18 in each instance comprise one or more permanent magnets, the interaction of which causes a radial position of a rotor axis 19, which corresponds to an axis of symmetry of the rotor 8, to be set. In preferred embodiments, the position of the rotor axis 19 is set during the production of the blood pump 2, as explained in greater detail below, such that the rotor axis 19 coincides, during operation, with an axis of symmetry (cylinder axis) of the flow channel 10. In this way, a distance 20 or a gap between the blading 11, 11' and the delimitation 16 of the flow channel 10 may also be precisely set. In preferred embodiments, this distance is smaller than 500 μm, for example 100 μm.

In some embodiments, the rotor 8 is held in position and thus mounted also in the axial direction by the shown device. For this purpose, the electric motor 6 may also have a contact bearing 21, for example a tapered bearing or a ball bearing, with limits movement of the rotor 8 in or against the flow direction 12. It may additionally be provided that the stator bearing magnet 17, in order to axially bias the rotor 8, acts on the rotor bearing magnet 18 such that the rotor 8, in particular in the idle position, i.e. when the rotor 8 is not being driven, is pressed against the contact bearing 21. The pressure of the rotor 8 on the contact bearing 21 may be reduced during operation of the blood pump 2 by a thrust of the rotor 8, so that the rotor 8 is mounted axially with little friction. The method, described in detail further below, for producing the blood pump 2 is preferably applicable to the passive magnetic radial bearing described here. However, it may also be applied advantageously to, for example, other bearing types provided additionally or alternatively, for example axial bearings. In addition, the production method may be applied advantageously both for axial pumps and the radial pumps.

If permanent magnets, such as ring magnets, are used to produce the stator 13 or the rotor 8, there may be deviations from a desired magnetic field distribution caused by these permanent magnets. Such manufacturing tolerances are not insignificant, in particular when blood pumps 2 with a small gap 20 in the flow channel 10 in the region of the rotor 8 are to be produced. A deviation of the magnetic properties of the stator bearing magnet 17 used during the production may, for example, cause an axis of symmetry of the magnetic field generated by the stator bearing magnets 17 to be radially shifted relative to the geometric axis of symmetry of the flow channel 10, that is to say for example to not lie on the cylinder axis of the flow channel 10. In addition, in the event of deviations of the rotor bearing magnet 18 from its desired magnetic properties, it may be, for example, that in access of inertia or a geometric axis of symmetry of the rotor 8 does not coincide with its magnetic center-of-gravity axis.

Undesirable deviations of this kind of the magnetic properties of the used permanent magnets may be corrected during the production of the blood pump 2, as is shown in FIGS. 3(*a*) to (*c*) in schematic views in the axial direction. The flow channel 10, in which the rotor 8 is received with the conveying element, is delimited by the inner wall 16 of the stator 13. In the shown example, an axis of inertia 22 of the rotor 8 coincides with the geometric axis of symmetry 19 of the rotor. If the axis of inertia 22 of the rotor 8 in other embodiments does not coincide with the geometric axis of symmetry of the rotor, i.e. if a mechanical unbalances present, mass corrections of the mechanical unbalance may be made in a manner known per se. However, the axis of inertia 22 of the rotor 8, often fails to coincide with a magnetic center-of-gravity axis 23 of the rotor 8 due to the above-described manufacturing tolerances of the used permanent magnet 18, which results in a magnetic unbalance of the rotor 8.

If the electric motor 6 of the blood pump 2 is operated at low speeds, the magnetic unbalance of the rotor 8 comes into effect, so that the rotor 8 does not rotate about its axis of inertia 22, but instead about its magnetic center-of-gravity axis 23. This results in a time-dependent rotor position in the form of a wobbling, vibratory or swaying movement of the rotor 8, in which the rotor 8 moves over a circle-like path in the pump tube, which is illustrated in FIG. 3(*a*) by the positions of the rotor 8', 8" wobbling in a clockwise direction in the shown example at different moments in time. If the rotor position is unstable, a deflection, i.e. a distance of the rotor 8 from the inner wall 16 of the stator 13 or a distance of the rotor 8 from the geometric axis of symmetry 24 of the flow channel 10, is time-dependent on account of the wobbling movement of the rotor 8.

When producing the electric motor 6 of the blood pump 2, the rotor 8 may firstly be arranged in the flow channel 10 delimited by the inner wall 16 of the stator 13. The electric motor 6 may then be driven, for example under conditions that correspond almost to the conditions that are present during operation when the blood pump 2 is in the implanted state. For example, when producing the electric motor 6, a liquid may be conveyed through the flow channel for test purposes. The rotor position may be monitored during production of the electric motor 6, whilst the rotor 8 is being driven in rotation, for example by being observed under a microscope or by use of distance sensors.

On the basis of an observation of the wobbling movement of the rotor 8 at low speeds, the magnetic properties of the rotor bearing magnet 18 may be corrected, as described below in greater detail. As a result of this correction, with may possibly comprise a number of iteration steps, the axis of inertia 22 of the rotor 8 may be brought into conformity with the magnetic center-of-gravity axis 23 of the rotor 8. As soon as this conformity has been achieved, the rotor 8 rotates at low speeds about the common axis of inertia and magnetic center-of-gravity axis 22, 23, as is illustrated in FIG. 3(*b*).

The rotational movement of the rotor 8 is self-stabilising with increasing speed, so that the rotor 8, at higher speeds, rotates about its axis of inertia 22, even if the magnetic properties of the rotor bearing magnet 18 have not been corrected, i.e. if the axis of inertia 22 of the rotor 8 does not coincide with the magnetic center-of-gravity axis 23 of the rotor. For example, at a nominal speed of the blood pump 2, i.e. at a speed at which the electric motor 6 is generally operated when the blood pump 2 is implanted in the patient in order to pump blood, the rotor 8 rotates in a self-stabilised manner. In this case, that is to say for self-stabilised rotation of the rotor 8 at high speeds, the situation shown in FIG. 3(*b*) thus likewise arises, with the rotor 8 rotating about its axis of inertia 22 with a stabilised rotor position.

If the rotor 8 rotates with a stable rotor position, it may be that the axis of rotation of the rotor 8 does not coincide with a desired rotor position on the axis of symmetry 24 of the flow channel 10 due to manufacturing tolerances in the magnetic properties of the stator 13 and in particular of the stator bearing magnet 17. An undesirable, temporally constant deflection of the rotor position in relation to the axis of symmetry 24 of the flow channel 10 may thus result with the stable rotor position.

By observing the deflection of the rotor position, the magnetic properties of the stator 13 or of the stator bearing magnet 17 may then be corrected, and again a number of iteration steps (observing the rotor position with subsequent correction of the magnetic properties, renewed observation of the rotor position, etc.) may be performed. In particular, the steps of determining the deflection and of making a correction may be performed repeatedly until the determined deflection of the rotor 8 falls below a defined target value. As a result of the correction of the magnetic properties of the stator 13, the axis of inertia 22, about which the rotor 8 is rotating, may be brought into conformity with the axis of symmetry 24 of the flow channel 10, as is shown in FIG. 3(*c*). In this way, it may be ensured that, during operation of the electric motor 6 of the blood pump 2 at nominal speed, the size of the gap 20 is precisely defined, which is useful in particular in the case of small embodiments of the blood pump 2. The magnetic properties of the stator 13 may be corrected, for example, by securing a magnetically active material 25, in particular a ferromagnetic material (for example a shimming iron ore sheet) in a quadrant of the stator 13, as is shown schematically in FIG. 3(*c*). However, further possibilities for correcting the magnetic properties of the stator 13 are also described above and below.

The electric motor 6 shown in FIG. 2 is corrected both in respect of the magnetic properties of the rotor 8 and in respect of the magnetic properties of the stator 13. The rotor 8, in the region of the rotor bearing magnet 18 and in the region of its cylindrical axis of symmetry 19, has a cylindrical opening 30, which for example is filled at least in part on one half side with a barmaid of a magnetically active material 26 and on one half side with a barmaid of magnetically inactive material 27. The magnetically active material 26 typically comprises ferromagnetic material, and for example may be a half-round iron bar. By means of the magnetically active material 26, the magnetic center-of-gravity axis 23 of the rotor 8 is brought into conformity with the axis of inertia 22 of the rotor 8 when correcting the magnetic properties of the rotor 8. The magnetically inactive material 27 is provided so that the correction does not give rise to a notable mechanical unbalance. The magnetically inactive material 27 may be a balancing mass, for example, and in particular may have practically the same density as the magnetically active material 26, so that the magnetic properties may be corrected relatively easily without generating a mechanical balance. The magnetically inactive material 26, in the present example, may be formed as a half-round bar made of non-magnetizable steel. In other embodiments, it would be possible additionally or alternatively that, when correcting the magnetic properties of the rotor 8, any pre-existing magnetically active material of the rotor bearing magnet 18 is removed in partial areas of a circumference of the rotor 8, i.e. non-rotationally symmetrically, or is altered in respect of the magnetic properties (magnetized or demagnetized), for example by local heating by means of laser or soldering iron.

Figure 4:
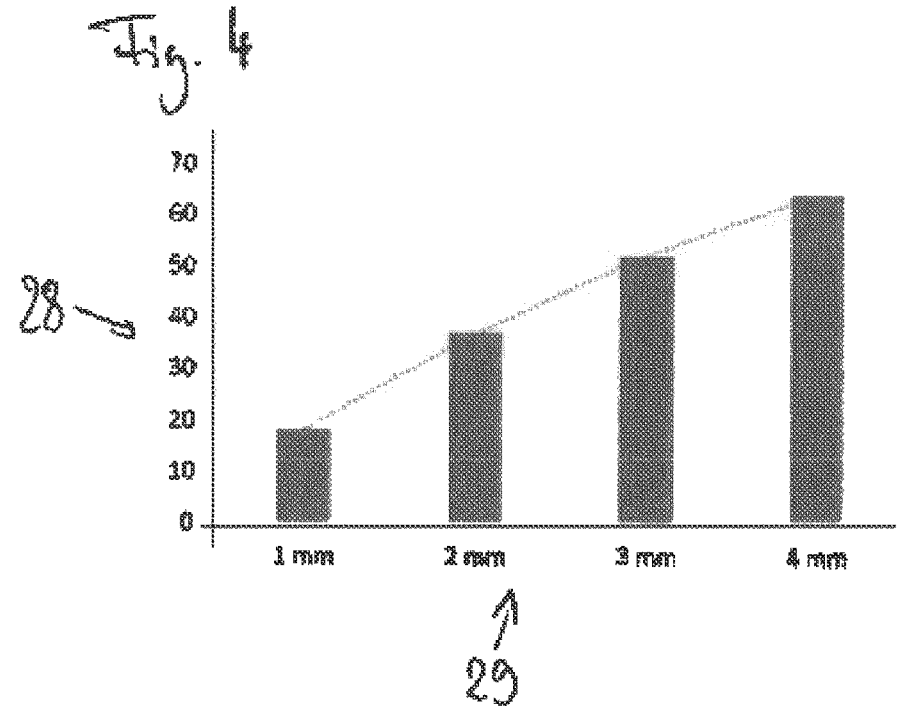
FIG. 4 shows an illustration of a correction of a rotor position of the electric motor.

The magnetic properties of the stator 13 are corrected in the shown example by applying the magnetically active material 25 to an outer side of the stator bearing magnet 17. FIG. 4 illustrates that the magnetic properties of the stator bearing magnet 17 may be corrected very effectively and in a targeted manner. What is plotted is a correction 28 of the above-described static deflection of the rotor position in μm, i.e. a displacement of the position of the axis of inertia of the rotor 8 in the direction of the axis of symmetry 24 of the flow channel, over an axial extent 29 of the shimming plate 25 with a thickness of 200 μm. For example, with an axial extent of the shimming plate 25 of 4 mm, a targeted correction of the rotor position of approximately 60 μm may be produced, for example. In other embodiments, it would be possible additionally or alternatively that, when correcting the magnetic properties of the stator 13, any pre-existing magnetically active material of the stator bearing magnet 17 is removed in partial areas of a circumference of the stator 13, i.e. non-rotationally symmetrically, or is altered in respect of the magnetic properties (magnetized or demagnetized), for example by local heating by means of laser or soldering iron.

Only features of the various embodiments disclosed in the embodiment examples may be combined with one another and claimed individually.

To clarify the use of and to hereby provide notice to the public, the phrases "at least one of <A>, <B>, . . . and <N>" or "at least one of <A>, <B>, . . . or <N>" or "at least one of <A>, <B>, . . . <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The invention claimed is:

1. A method for producing a bearing arrangement for an implantable blood pump, comprising:
   providing a rotor having one or more drive magnets, wherein the rotor has a conveying element,
   providing a stator having stator windings,
   arranging the rotor in a flow channel formed by an inner wall of the stator,
   driving the rotor in rotation,
   determining a deflection of the rotor while the rotor is being driven in rotation,
   correcting the deflection of the rotor by:
      non-rotationally symmetrical application of magnetically active material on the stator, and/or
      non-rotationally symmetrical application of magnetically active material on the rotor having one or more drive magnets, and/or
      non-rotationally symmetrical removal of magnetically active material from the stator, and/or
      non-rotationally symmetrical removal of magnetically active material from a drive magnet of the rotor.

2. The method of claim 1, wherein the bearing arrangement forms a passive magnetic bearing.

3. The method of claim 1, wherein the method is performed outside of a body of a human or animal.

4. The method of claim 1, comprising:
   delivering a pump which contains the corrected bearing arrangement, and/or packaging in a sterile manner a blood pump which contains the corrected bearing arrangement.

5. The method of claim 1, wherein the deflection of the rotor is determined by means of microscope and/or by means of distance sensors while the rotor is being driven in rotation.

6. The method of claim 1, wherein the deflection of the rotor is corrected by non-rotationally symmetrical application or removal of magnetically active material on the rotor, and magnetically inactive material is additionally removed from the rotor or applied to the rotor to correct a mechanical unbalance of the rotor.

7. A method for producing a bearing arrangement for an implantable blood pump, comprising:

providing a rotor having one or more drive magnets, wherein the rotor has a conveying element, providing a stator having stator windings, arranging the rotor in a flow channel formed by an inner wall of the stator, driving the rotor in rotation, determining a deflection of the rotor while the rotor is being driven in rotation, correcting the deflection of the rotor by permanent magnetization or permanent demagnetization of magnetically active material on at least one of the stator and the rotor.

8. The method of claim 7, wherein the bearing arrangement forms a passive magnetic bearing.

9. The method of claim 7, wherein the magnetically active material is permanently magnetized or permanently demagnetized on the rotor during the correction.

10. The method of claim 7, wherein the method is performed outside of a body of a human or animal.

11. The method of claim 7, comprising:

delivering a pump which contains the corrected bearing arrangement, and/or packaging in a sterile manner a blood pump which contains the corrected bearing arrangement.

12. The method of claim 7, wherein the deflection of the rotor is determined by means of microscope and/or by means of distance sensors while the rotor is being driven in rotation.

* * * * *